(12) United States Patent
Dana et al.

(10) Patent No.: US 7,842,051 B2
(45) Date of Patent: *Nov. 30, 2010

(54) SNARED SUTURE TRIMMER

(75) Inventors: Mike Dana, San Jose, CA (US); Rob George, San Jose, CA (US); T. Daniel Gross, Los Gatos, CA (US); Maurice Marthaler, Santa Rosa, CA (US); Dawn Ma, San Jose, CA (US); Jim Swett, Fremont, CA (US)

(73) Assignee: Abbott Laboratories, Abbott Park, IL (US)

( * ) Notice: Subject to any disclaimer, the term of this patent is extended or adjusted under 35 U.S.C. 154(b) by 749 days.

This patent is subject to a terminal disclaimer.

(21) Appl. No.: 11/461,243

(22) Filed: Jul. 31, 2006

(65) Prior Publication Data

US 2006/0264977 A1 Nov. 23, 2006

Related U.S. Application Data

(60) Continuation of application No. 10/860,443, filed on Jun. 3, 2004, now Pat. No. 7,147,646, which is a division of application No. 10/004,817, filed on Dec. 7, 2001, now Pat. No. 6,746,457.

(51) Int. Cl.
  *A61B 17/04* (2006.01)
(52) U.S. Cl. ...................................... 606/148
(58) Field of Classification Search ........................ None
  See application file for complete search history.

(56) References Cited

U.S. PATENT DOCUMENTS

| | | | |
|---|---|---|---|
| 3,328,876 A | 7/1967 | Hoppe | |
| 3,372,477 A | 3/1968 | Hoppe | |
| 3,380,448 A | 4/1968 | Sadove et al. | |
| 3,625,556 A | 12/1971 | Stromberg | |

(Continued)

FOREIGN PATENT DOCUMENTS

DE  9112301  1/1992

(Continued)

OTHER PUBLICATIONS

PCT/US02/39151 International Search Report.

(Continued)

*Primary Examiner*—Kevin T Truong
(74) *Attorney, Agent, or Firm*—Workman Nydegger

(57) ABSTRACT

A suture trimmer, the suture trimmer including a shaft having a first end, a second end and a bore extending axially therebetween, the shaft having an opening formed in the side adjacent the distal end. A fitting is on the distal end of the shaft, the fitting having an aperture formed therethrough, the aperture axially aligned with the bore of the lumen and in communication with the opening formed in the shaft. The suture trimmer further including a actuating device, the actuating device coupled to a cutting member slidably disposed within the bore of the shaft, the cutting member configured to be moved between a first position and a second position, when disposed in the second position the cutting member closes the opening formed in the side of the shaft.

15 Claims, 8 Drawing Sheets

U.S. PATENT DOCUMENTS

| | | |
|---|---|---|
| 3,752,516 A | 8/1973 | Mumma |
| 3,840,017 A | 10/1974 | Violante |
| 4,246,698 A | 1/1981 | Lasner et al. |
| 4,369,787 A | 1/1983 | Lasner et al. |
| 4,527,331 A | 7/1985 | Lasner et al. |
| 4,602,635 A | 7/1986 | Mulhollan |
| 4,641,652 A | 2/1987 | Hatterer |
| 4,957,498 A | 9/1990 | Caspari et al. |
| 4,961,741 A | 10/1990 | Hayhurst |
| 5,059,201 A | 10/1991 | Asnis |
| 5,133,723 A | 7/1992 | Li |
| 5,176,691 A | 1/1993 | Pierce |
| 5,176,695 A | 1/1993 | Dulebohn |
| 5,242,459 A | 9/1993 | Buelna |
| 5,269,791 A | 12/1993 | Mayzels et al. |
| 5,292,327 A | 3/1994 | Dodd |
| 5,304,190 A | 4/1994 | Reckelhoff et al. |
| 5,312,423 A | 5/1994 | Rosenbluth et al. |
| 5,342,459 A | 8/1994 | Klemp et al. |
| 5,403,330 A | 4/1995 | Tuason |
| 5,405,351 A | 4/1995 | Kinet |
| 5,405,354 A | 4/1995 | Sarrett |
| 5,417,699 A | 5/1995 | Klein |
| 5,423,837 A | 6/1995 | Mericle |
| 5,520,702 A | 5/1996 | Sauer et al. |
| 5,527,322 A | 6/1996 | Klein et al. |
| 5,549,618 A | 8/1996 | Fleenor et al. |
| 5,565,122 A | 10/1996 | Zinnbauer et al. |
| 5,585,122 A | 12/1996 | Drum et al. |
| 5,643,289 A | 7/1997 | Sauer et al. |
| 5,649,939 A | 7/1997 | Reddick |
| 5,669,917 A | 9/1997 | Sauer et al. |
| 5,704,943 A | 1/1998 | Yoon |
| 5,746,752 A | 5/1998 | Burkhart |
| 5,797,928 A | 8/1998 | Kogasaka |
| 5,797,929 A | 8/1998 | Andreas et al. |
| 5,830,234 A * | 11/1998 | Wojciechowicz et al. ... 606/224 |
| 5,860,993 A | 1/1999 | Thompson |
| 5,879,371 A | 3/1999 | Gardiner et al. |
| 5,997,555 A | 12/1999 | Kontos |
| 6,004,295 A | 12/1999 | Langer et al. |
| 6,007,544 A | 12/1999 | Kim |
| 6,007,554 A | 12/1999 | Van Ess |
| 6,045,570 A | 4/2000 | Epstein |
| 6,051,004 A | 4/2000 | Gill |
| 6,077,279 A | 6/2000 | Kontos |
| 6,132,439 A | 10/2000 | Kontos |
| 6,171,317 B1 | 1/2001 | Jackson et al. |
| 6,254,620 B1 | 7/2001 | Koh |
| 6,261,272 B1 | 7/2001 | Gross et al. |
| 6,527,785 B2 | 3/2003 | Sancoff et al. |
| 6,620,185 B1 | 9/2003 | Harvie et al. |
| 6,733,509 B2 | 5/2004 | Nobles |
| 6,746,457 B2 | 6/2004 | Dana et al. |
| 6,860,890 B2 | 3/2005 | Bachman |
| 7,094,246 B2 | 8/2006 | Anderson |
| 7,147,646 B2 | 12/2006 | Dana et al. |
| 2003/0120287 A1 | 6/2003 | Gross et al. |
| 2003/0181926 A1 | 9/2003 | Dana |
| 2006/0293700 A1 | 12/2006 | Dana |

FOREIGN PATENT DOCUMENTS

| | | |
|---|---|---|
| DE | 9214580 | 4/1994 |
| EP | 0669103 | 8/1995 |
| WO | WO 94/08515 | 4/1994 |
| WO | WO 95/32669 | 12/1995 |
| WO | WO 00/69342 | 5/2000 |
| WO | WO 02/15795 | 2/2002 |
| WO | WO 03/049621 | 6/2003 |
| WO | WO 03/059174 | 7/2003 |

OTHER PUBLICATIONS 6,746,457, Office Action, mail date Dec. 18, 2002.
6,746,457, Notice of Allowance, mail date Jul. 28, 2003.
6,746,457, Notice of Allowance, mail date Feb. 4, 2004.
6,746,457, Issue Notification, mail date May 20, 2004.
7,094,246, Office Action, mail date Aug. 31, 2005.
7,094,246, Notice of Allowance, mail date Feb. 23, 2006.
7,094,246, Issue Notification, mail date Aug. 2, 2006.
7,147,646, Office Action, mail date May 17, 2006.
7,147,646, Notice of Allowance, mail date Oct. 2, 2006.
7,147,646, Issue Notification, mail date Nov. 22, 2006.
2003/0120287, Office Action, mail date Jun. 2, 2003.
2003/0120287, Office Action, mail date Dec. 8, 2003.
2003/0120287, Office Action, mail date May 28, 2004.
2003/0120287, Office Action, mail date Oct. 23, 2006.
2003/0120287, Office Action, mail date Apr. 17, 2007.
2003/0181926, Office Action, mail date Mar. 27, 2006.
2003/0181926, Office Action, mail date Aug. 8, 2006.
2003/0181926, Office Action, mail date Jan. 29, 2007.
2003/0181926, Notice of Allowance, mail date Aug. 30, 2007.
U.S. Appl. No. 10/027,681, mail date Jul. 8, 2009, Office Action.

* cited by examiner

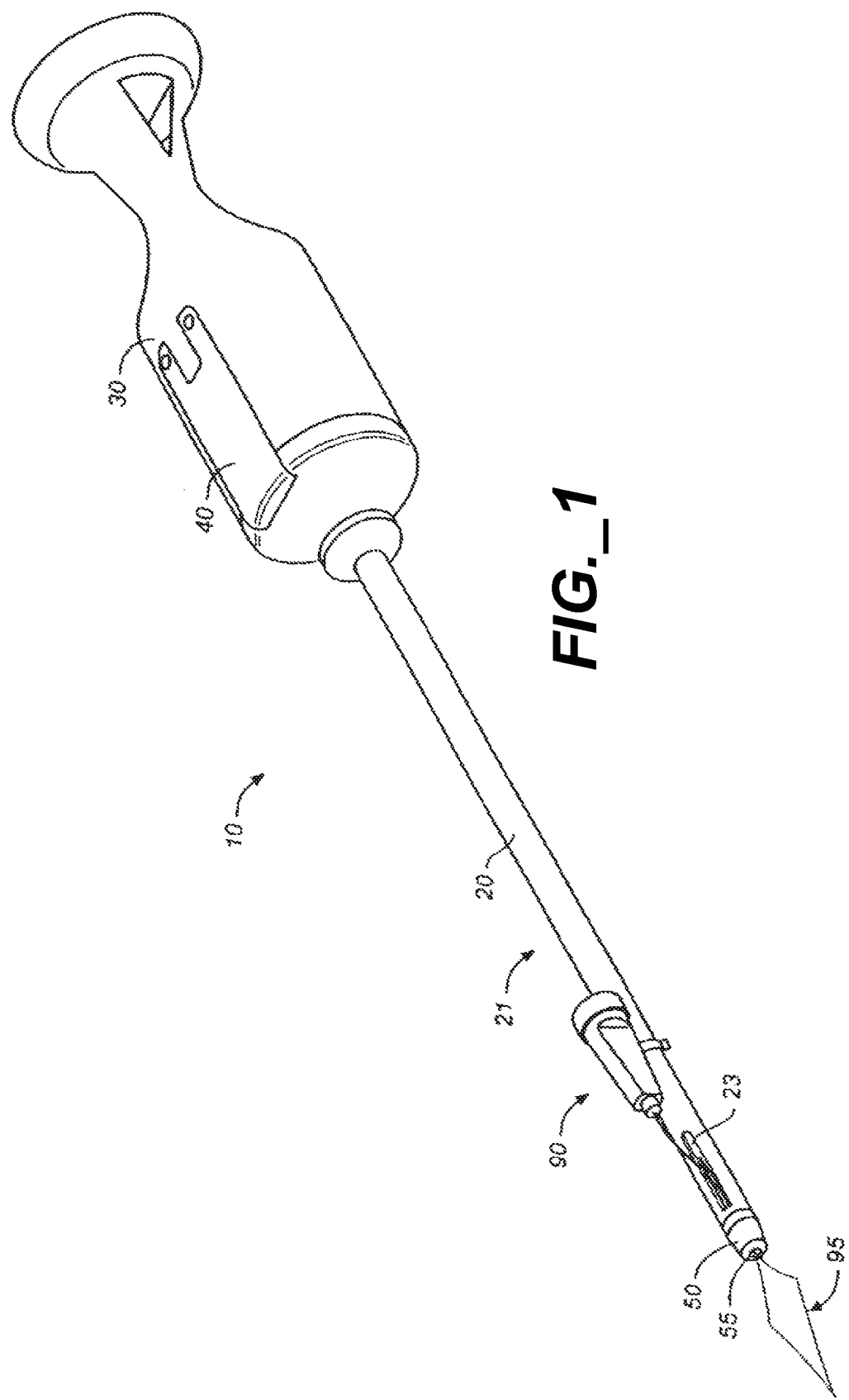

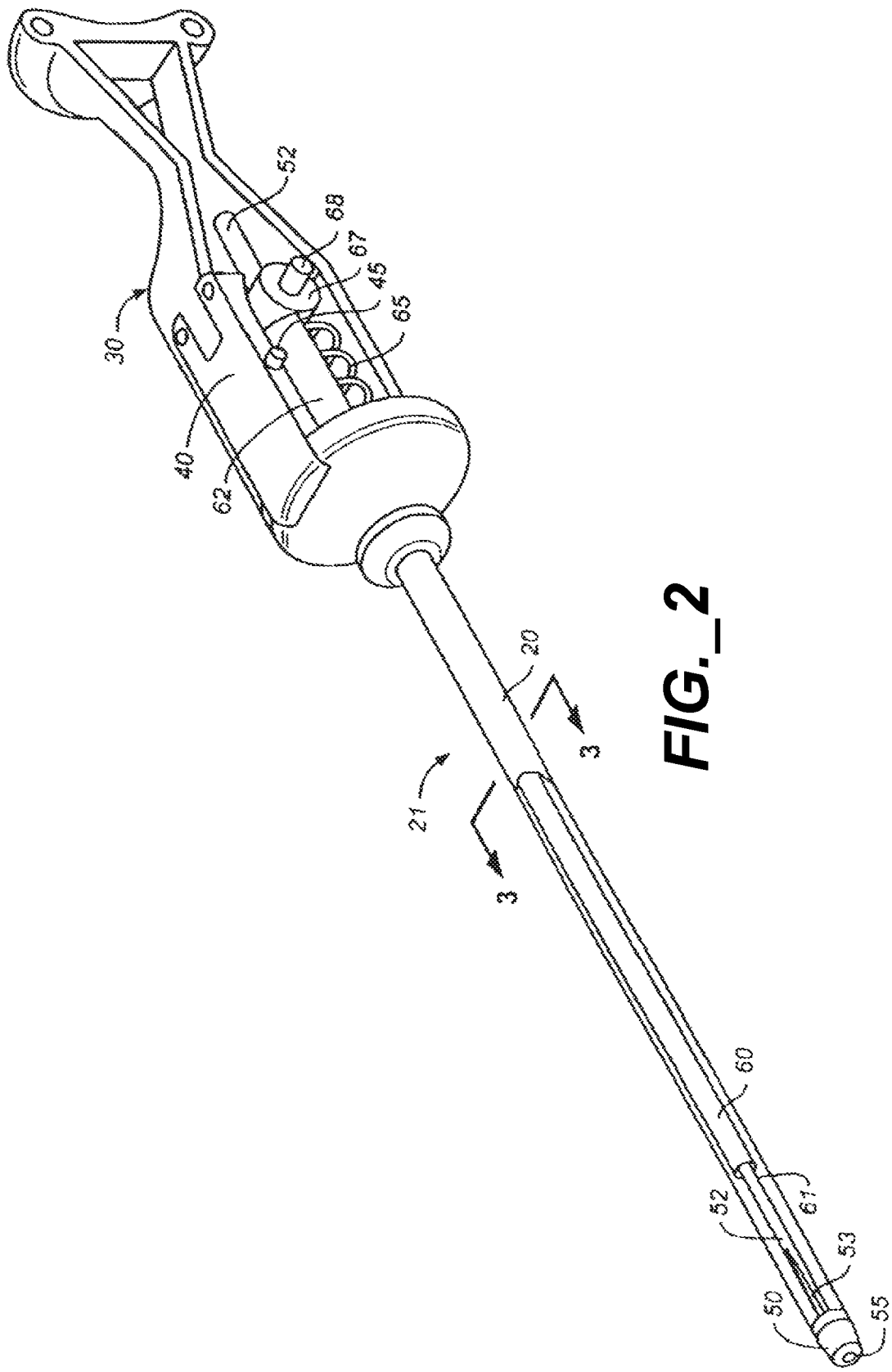
FIG._2

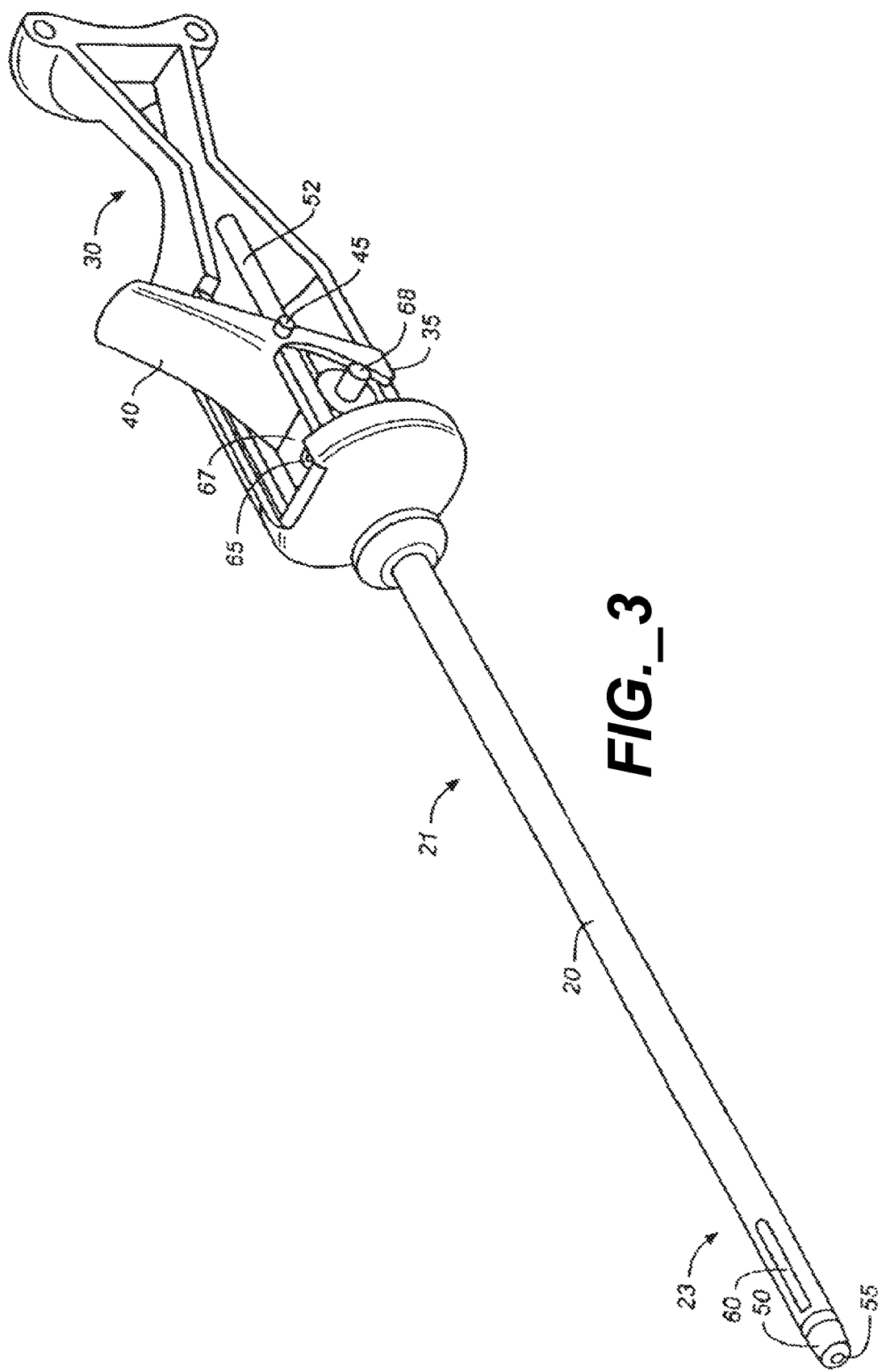

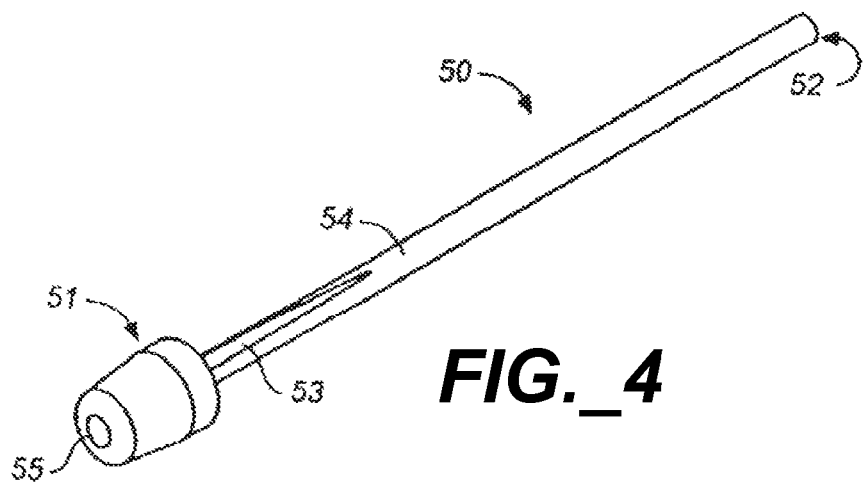
FIG._4
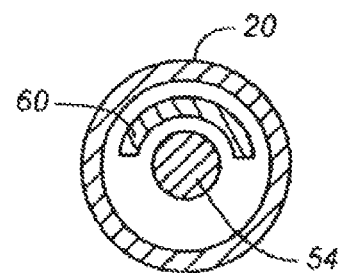
FIG._5
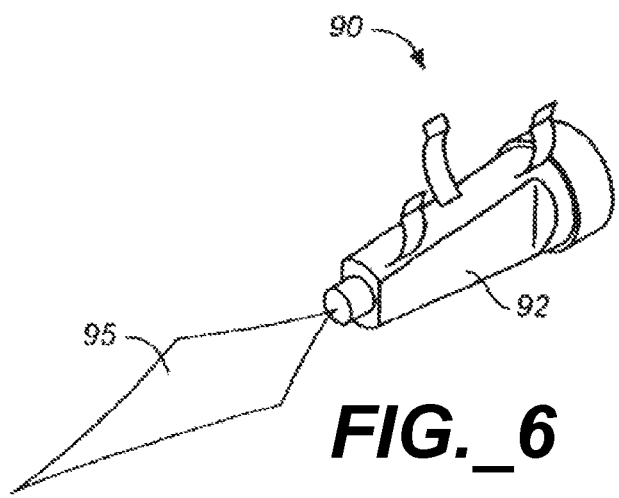
FIG._6

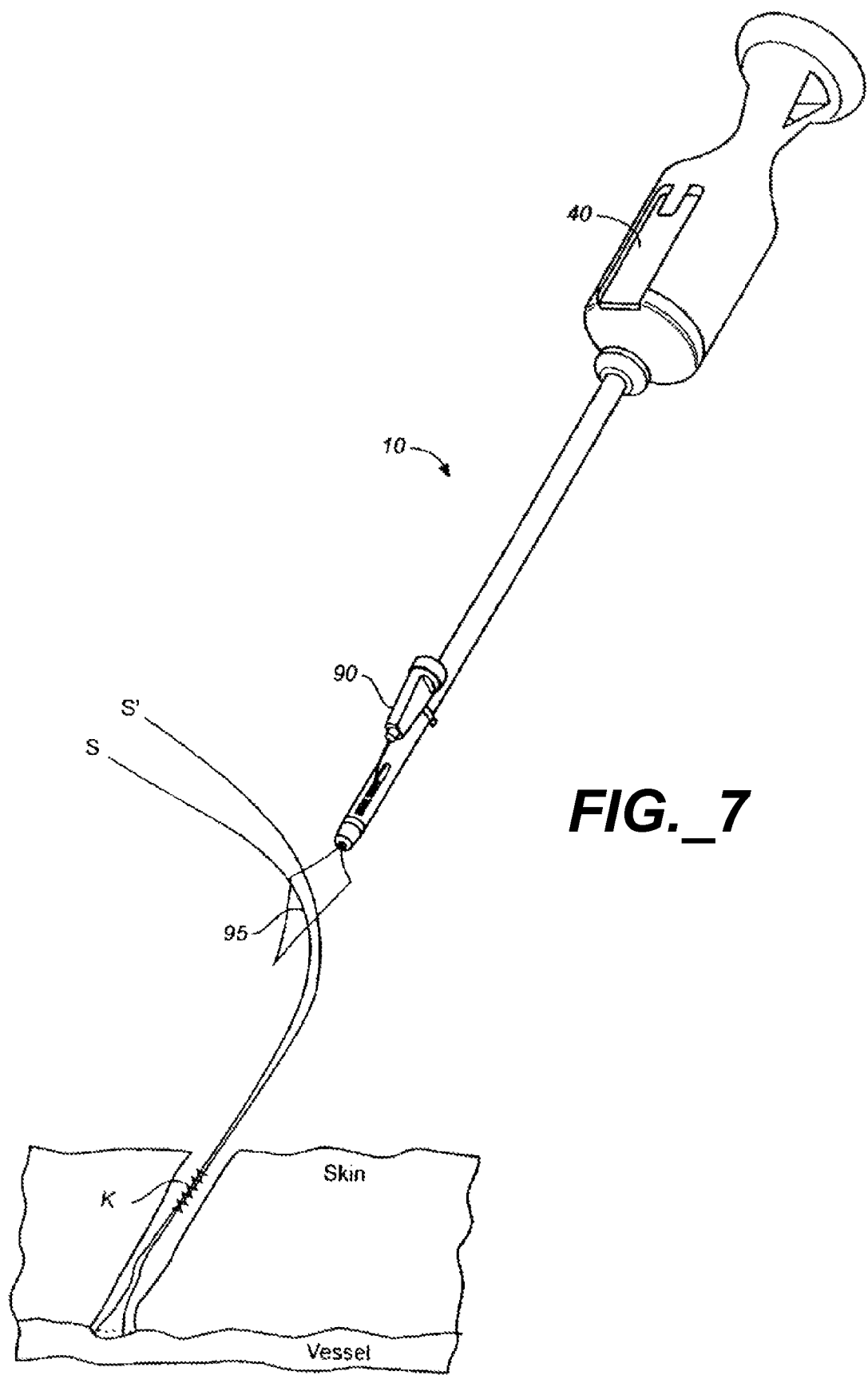
FIG. _7

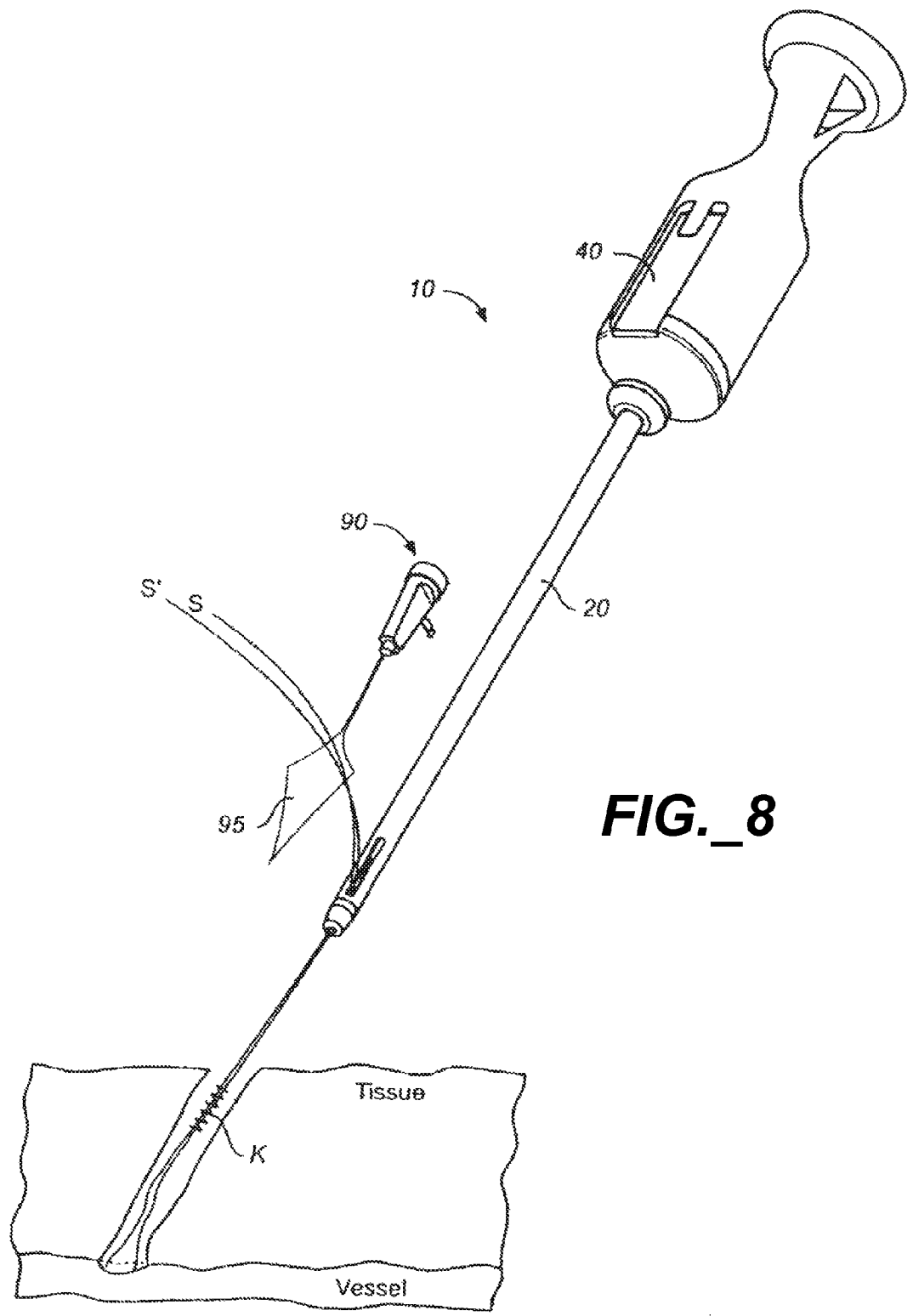
FIG._8

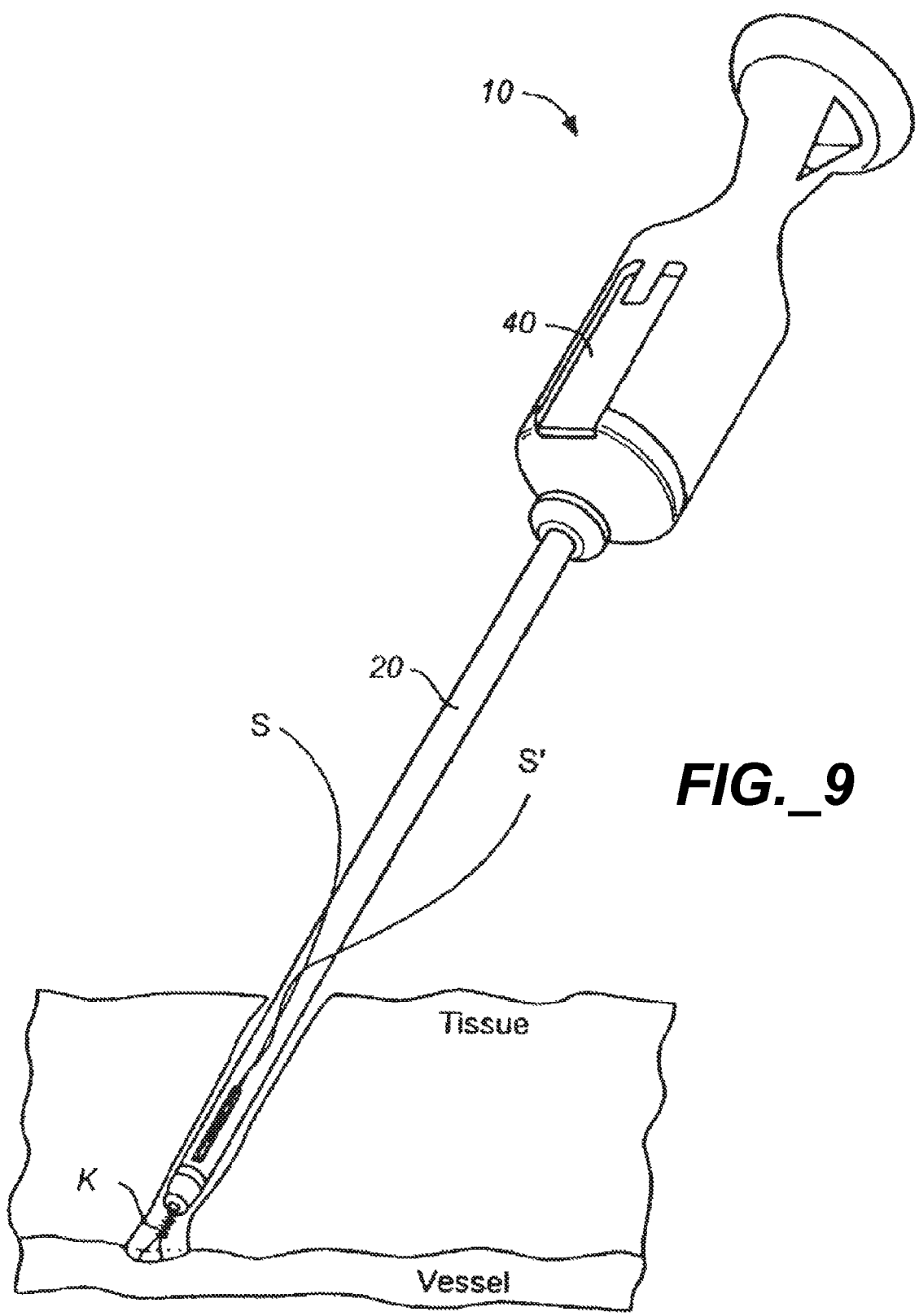
FIG._9

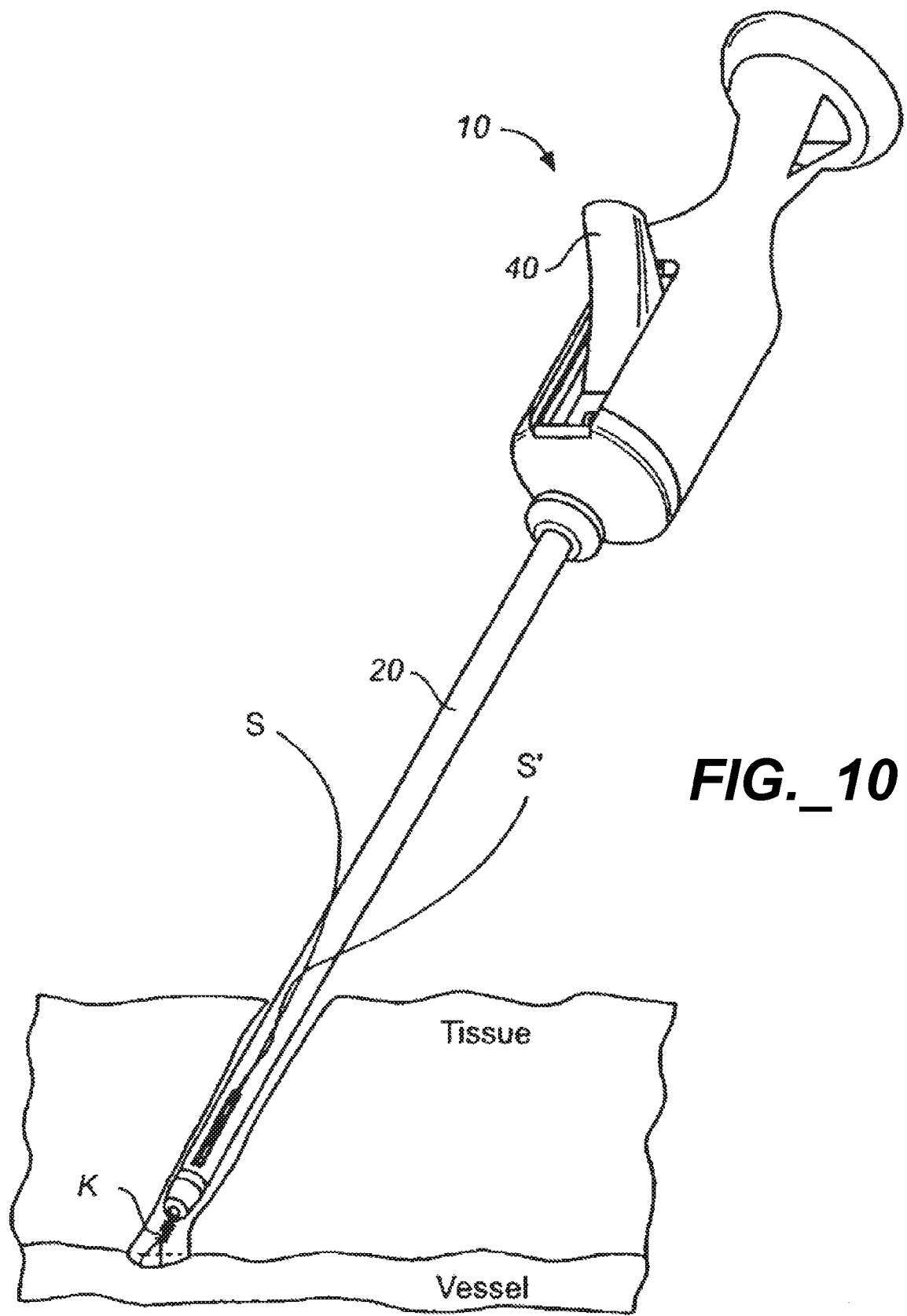
FIG._10

SNARED SUTURE TRIMMER

CROSS-REFERENCE TO RELATED APPLICATIONS

This is a continuation of U.S. patent application Ser. No. 10/860,443, filed Jun. 3, 2004, and entitled "Snared Suture Trimmer", which is a divisional application of U.S. patent application Ser. No. 10/004,817, filed Dec. 7, 2001, and entitled "Snared Suture Trimmer", now issued as U.S. Pat. No. 6,746,457, the disclosures of each are incorporated herein by this reference.

BACKGROUND OF THE INVENTION

1. The Field of the Invention

The present invention relates generally to surgical devices and methods. More particularly, the present invention relates to the construction and use of devices for advancing surgical knot(s) and trimming the ends of the suture adjacent to the knot(s). Such a device is to be referred to as a "suture trimmer", as used through the appended specification.

2. The Relevant Technology

The closing of incision and wounds using suture is a preferred technique of surgeons and many other physicians. While other techniques are now available such as stapling, the use of "tissue glues," and the use of collagen for closing vascular punctures, the use of suture is often preferred because it provides a reliable and tight closure of any wound. Additionally, if a suture is to fail, the surgeon will know immediately, this is unlike many of the other devices listed above which may not fail until some time after the procedure.

While the suturing of a wound is a relatively straight forward procedure in most open surgical procedures, placement and tying of sutures in laparoscopic and other minimally invasive procedures can be problematic. In order to provide for suturing under such circumstances, a variety of devices have been developed for the remote placement and tying of suture through cannulas under video observation. Usually, a sliding knot will be formed in a suture loop, a tool known as a "knot pusher" such as that shown in U.S. Pat. No. 5,797,929 the entirety of which is hereby incorporated by reference, is utilized to advance and position the knot and tighten the loop of suture.

Such knot pushing devices may also be utilized in recently developed techniques for the remote suturing of vascular punctures. Punctures may be formed in the femoral or other arteries to provide vascular access for performing angioplasty and other vascular procedures. Such techniques are described in U.S. Pat. No. 5,417,699 and U.S. Pat. No. 5,527,322, the entireties of which are hereby incorporated by reference. Such methods result in the placement of a suture loop through tissue on opposite sides of the vascular puncture. Two free ends of the suture loop are brought out through a tissue tract leading to the puncture, and the ends may be externally tied by the treating physician. Alternatively, a knot forming device such as that shown in U.S. Pat. No. 6,171,317, the entirety of which is hereby incorporated by reference, may be utilized to tie a knot.

Through the use of a knot pusher, such as that shown and described in U.S. Pat. No. 5,797,929, the entirety of which is hereby incorporated by reference, the knot may be advanced through the tissue tract so that it lies directly over the adventitial wall of the blood vessel.

After the knot has been advanced over the adventitial wall of the blood vessel and tightened, the excess suture must be cut away. Typically, a surgeon may utilize a scalpel or a pair of scissors to cut the suture ends just below the exterior surface of the patient's skin.

A concern with this method is that by leaving lengths of suture within the wound may lead to irritation of the incision. More significantly, a relatively long suture end, extending from the knot at the vessel repair to the skin level, may act as a "wick" for infective microorganisms which may be present at skin level. The wick would provide a conduit for these microorganisms to travel from the skin surface to the vessel repair, thereby leading to infection. Many times a surgeon cannot easily shorten this cut length because the location of the knot is well below the patient's tissue and is not readily visible, therefore they can only shorten the suture to the point that they can visually see. Further still, many surgical procedures are moving away from being open and toward being minimally invasive wherein the procedure is performed within a small opening formed in the patient's tissue. As described above, many times the surgeon cannot see the vessel which they are trying to close with the suture.

Therefore there is a need for a device that will enable a surgeon to advance a knot and trim the excess suture from the knot without having to visually see the knot.

BRIEF SUMMARY OF THE INVENTION

In one aspect of the invention there is provided a suture trimmer, the suture trimmer including a shaft having a first end, a second end and a bore extending axially therebetween, the shaft having an opening formed in the side adjacent the distal end. A fitting disposed on the distal end of the shaft, the fitting having an aperture formed therethrough, the aperture axially aligned with the bore of the lumen and in communication with the opening formed in the shaft. The suture trimmer further includes a housing disposed on the proximal end of the shaft, the housing including a lever and biasing device, the lever coupled to a cutting member slidably disposed within the bore of the shaft, the cutting member configured to be moved between a first position and a second position, when disposed in the second position the cutting member closes the opening formed in the side of the shaft.

In another aspect of the invention there is provided a method for closing a suture loop, the method including the steps of tensioning a suture loop, the suture loop disposed within a patient and having two free ends and a knot disposed on one of the free ends. The method further includes disposing the two free ends of the suture through a suture trimming device. The method may further include the step of advancing a distal end of the suture trimming device to contact the knot and advance the knot to close the suture loop while holding at least one end of the suture, and activating a cutting member within the suture trimmer to cut the two free ends of the suture adjacent to the knot.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 1 is a isometric view of an exemplary embodiment of a suture trimmer in accordance with the present invention;

FIG. 2 is a partial cut-away isometric view of an exemplary embodiment of the suture trimmer in accordance with the present invention;

FIG. 3 is a partial cut-away isometric view of an exemplary embodiment of the suture trimmer in accordance with the present invention wherein the cutting member has been deployed;

FIG. 4 is a isometric view of an exemplary embodiment of a fitting in accordance with the present invention;

FIG. 5 is a cross-sectional view of the shaft, fitting, and cutting member of the suture cutter in accordance with the present invention;

FIG. 6 is a isometric view of a suture snare in accordance with the present invention;

FIG. 7 is a isometric view of the suture trimmer in accordance with the present invention wherein two free suture ends are disposed through the suture snare;

FIG. 8 is an isometric view of the suture trimmer in accordance with the present invention illustrating the two free suture ends as disposed through fitting and exiting through an opening formed in the shaft;

FIG. 9 is an isometric view of the suture trimmer according to the present invention wherein the tip of the suture trimmer is being utilized to advance at least one knot formed in the two free ends of the suture; and FIG. 10 is an isometric view of the suture trimmer in accordance with the present invention wherein the cutting member has been deployed to cut the two free ends of the suture.

DETAILED DESCRIPTION OF THE PREFERRED EMBODIMENTS

In accordance with the present invention there is provided a suture trimmer, the suture trimmer may be utilized by physicians in any of a variety of surgical procedures where suture loop has been formed in tissue to close an incision or wound, or for any other purpose. A slidable knot will be formed in the loop, and the suture trimmer is used to engage and advance the knot over a free end of the suture to close the loop. The knot can then be tightened by pulling on the other free end of the suture. The free ends of the suture may then be trimmed adjacent to the knot by activating the cutting member of the suture trimmer.

The suture trimmer in accordance with the present invention comprises an elongated, narrow diameter shaft suitable for use in remote procedures performed through percutaneous tissue punctures, such as vascular closures, laproscopic and other minimally invasive procedures and the like. Thus, the shaft of the suture trimmer may be embodied in many lengths to accommodate the various procedures for which the device may be utilized. The diameter of the shaft will be sufficiently small to facilitate the introduction through access sheaths, trocars, and the like, as well as punctures through the tissue of a patient's body, herein referred to as a "tissue tract." Typically the diameter of the shaft will range from about 4 French to about 10 French, more preferably the diameter of the shaft may range from about 6 French to about 8 French. The distal end of the shaft configured to engage and advance a slidable knot. A housing may be provided on the proximal end of the shaft wherein the housing forms a handle and retains a mechanism for activating the cutting member disposed in the shaft.

It shall be appreciated that although the suture trimmer has been described as being utilized in minimally invasive procedures, it is contemplated that the suture trimmer may be utilized for many open procedures that utilize suture to close vessels or wounds.

In a preferred embodiment a fitting will be provided at the distal end of the shaft. The fitting is preferably formed of a relatively hard material to firmly engage the knot and permit smooth advancement of the knot. The fitting is typically a cylindrical element having a flat or slightly convex or concave front face. The fitting preferably has a diameter equal to or less than the diameter of the shaft. The fitting will further included an aperture formed through an axis thereof and in communication with a opening formed in the side of the shaft. The free ends of the suture may be drawn through the aperture and opening through the use of a suture snare. Alternatively, the fitting may include a groove in communication with the aperture and the opening formed in the shaft. The free ends of the suture may be received in the groove and drawn therethrough, wherein, the free ends of the suture extend from the opening formed in the shaft, thereby eliminating the need for a snare. A locking mechanism may be deployed to retain the suture within the groove. The free ends of the suture extending from the opening formed in the shaft enable the tensioning of the knot after advancement of the knot. In an alternative embodiment, the structure of the fitting described herein may be integral with or formed from the shaft material such that a separate fitting piece can be eliminated from the assembly of the suture trimmer.

The shaft of the suture trimmer in accordance with the present invention is preferably rigid, typically being formed from of a bio-compatible material such as metal or plastic. Suitable metals include stainless steel, gold plated metals, silver plated metals, platinum or platinum plated metals, or titanium. It shall be understood that other metals may be utilized if an appropriate bio-compatible coated was applied thereto. Suitable plastics include polycarbonate, polyvinyl chloride (PVC), nylon, or similar plastics. As will be described in greater detail below, the shaft may be formed of more than one component. It is further contemplated that the shaft may be constructed to provide a degree of flexibility which will enable the device to be utilized in a greater number of surgical procedures.

The housing may be constructed of a bio-compatible material such as metal or plastic. Suitable metals include stainless steel, gold plated metals, silver plated metals, platinum or platinum plated metals, or titanium. It shall be understood that other metals may be utilized if an appropriate bio-compatible coated was applied thereto. Suitable plastics include polycarbonate, polyvinyl chloride (PVC), nylon, or similar plastics. In a preferred embodiment the housing is constructed of plastic.

Referring now to FIG. 1 there is shown an exemplary embodiment of the suture trimmer in accordance with the present invention. As shown in FIG. 1, the suture trimmer 10 comprises a shaft assembly 21, a housing 30, a fitting 50, and a suture snare 90. Each of which will be described in greater detail below with respect to the appropriate figures.

Referring now to FIG. 2, there is shown a partial cut-away view of an exemplary embodiment of the suture trimmer 10 in accordance with the present invention. As shown, the shaft assembly 21 comprises an outer shaft 20, a cutting member 60 slidably disposed therein and a fitting 50 disposed on the distal tip. Referring now to FIG. 1, the outer shaft 20 further includes an opening 23 formed in the side thereof adjacent to the distal tip. The proximal end of the shaft assembly 21 is received within a housing 30. The housing further including a biasing member 65 and a cutting member actuating device 40. The biasing member 65 is operatively coupled to the cutting member 60, thereby retaining the cutting member in a retracted position. The cutting member actuating device 40 advances the cutting member 60 within the bore of the shaft, wherein the cutting member extends to cover the opening formed in the side of the shaft and to sever suture projecting therefrom.

As shown in FIG. 5, the cutting member 60 may comprise a semi-circular or circular member disposed about the protrusion 54 of the fitting 50. Referring now to FIG. 2, the cutting member 60 includes a proximal end 62 and a distal end 61, the distal end being configured to sever suture. As shown in FIG. 2, a bushing 67 is disposed about the proximal end 62 of the cutting member 60. The bushing 67 retains the biasing member 65 within the housing 50. The bushing further includes at least one protrusion 68 extending therefrom and perpendicular to the axis of the shaft. The protrusion 68 is configured to engage the cutting member actuating device 40 disposed within the housing 50 as shown in FIG. 3.

Referring now to FIG. 3 there is shown the suture trimmer 10 in accordance with the present invention wherein the cutting member actuating device 40 has been actuated, thereby advancing the distal end of the cutting member across the opening 23 of the shaft 21. As shown in FIGS. 2 and 3, the cutting member actuating device 40 has a proximal end and a distal end. The proximal end being configured to engage the protrusions 68 extending from the bushing 67. The distal portion of the actuating device 40 may include a depressed or sculpted area configured to receive a user's finger, thereby providing a more positive grip on the actuating device. The actuating device 40 further includes a pivot pin 45. The pivot pin 45 is adapted to engage a portion 35 of the main housing 30, wherein the portion 35 of the main housing rotatably receives the pivot pin 45 thereby allowing the actuating device 40 to pivot about the portion 35.

Referring now to FIG. 4, there is shown an exemplary embodiment of the fitting 50 in accordance with the present invention. The fitting 50 includes distal end portion 51 having a protrusion 54 extending therefrom, the protrusion forming a proximal end portion 52. The protrusion further includes a skive or relieved area 53 formed adjacent to the distal end portion. An aperture 55 is formed axially within the distal end portion 51, wherein the aperture 55 is in communication with the skive 53. As described above, the end portion of the distal end 51 is configured to engage the knot and permit smooth advancement of the knot. The fitting 50 is typically a cylindrical element having a flat or slightly convex or concave front face. In an alternative embodiment, the face may be disposed at an angle relative to the axis of the shaft. The distal end 51 of fitting 50 preferably has a diameter equal to or less than the diameter of the shaft.

Referring now to FIG. 5 there is shown a cross sectional view of the shaft assembly 21 in accordance with the present invention. As shown, the shaft assembly comprises the outer shaft 20, the cutting member 60, and the protrusion 54 of the fitting 50. Although the elements are shown and described as being co-axially arranged, it is contemplated that the elements may be disposed in any manner within the outer sheath. Furthermore, it is contemplated that the outer sheath may be embodied having different geometric shapes such as oval, square, or generally circular as shown.

Referring now to FIG. 6, there is shown a suture snare in accordance with the present invention. The suture snare comprises a housing and a snare extending therefrom. As shown in FIGS. 1 and 6, the housing 92 has a proximal end and a distal end and is configured to be detachably attached to the shaft 20 of the suture trimmer 10. The snare 95 extends from the distal end of the housing 92. As shown the distal tip portion of the snare 95 is configured having a diamond shape, though many other geometric shapes may be utilized and the use of a diamond shaped distal tip shall be considered exemplary. The snare may be constructed of materials such as metal or plastic. Examples of suitable metals are stainless steel, copper, steel, titanium, platinum or nickel-titanium. Alternatively, a non-bio-compatible material may be utilized wherein the non bio-compatible material is then coated with a bio-compatible coating such as gold or silver. Examples of plastics that may be utilized are PVC, polyurethane, and similar plastics. In a preferred embodiment the snare is constructed of nickel-titanium wire. The use of nickel-titanium enables a larger distal end portion 92 than if conventional materials are utilized. Furthermore, the nickel-titanium will not deform or become deformed in normal use because of the shape memory characteristics of the material. The use of a larger distal section on the snare provides for easier loading of the sutures therein.

Referring now to FIGS. 7-10 there is shown the suture trimmer 10 in accordance with the present invention in use. As shown in FIG. 7, a suture loop including a knot has been formed in a vessel wall of a patient, the vessel wall having an opening, or arteriotomy, as a result of a medical procedure, for example. The two free ends of the suture are placed within the distal end portion 95 of the suture snare 90, wherein the distal end 95 of the snare has been disposed through the skive 23 and the aperture 55. The housing 92 being detachably mounted to the shaft 20 of the suture trimmer is removed from the shaft 20 and using a free hand the distal end of the snare 95 is drawn through the aperture 55 and the skive 23. As the snare is drawn through aperture and skive, the free ends of the suture S are additionally drawn through as shown in FIG. 8.

Referring now to FIG. 9 there is shown the end portion of the fitting contacting the knot K, wherein the knot is then advanced to the wound. One free end of the suture S is held tight to withdraw slack from the suture loop. The end portion of the fitting is utilized to place the knot tightly against the tissue, after the knot has been placed, the second free end of the suture S' is tensioned, thereby locking the knot.

Referring now to FIG. 10, the two free ends of the suture S and S' are taken into a free hand, the proximal end of the cutting member actuating device 40 is pressed, thereby pivoting the actuating device about the pivot pins. The surgeon then applies a force to the distal end of the actuating device. The applied force is transmitted through the actuating device to advance the cutting member from a retracted position within the shaft to an extended position as shown. The two free ends of the suture are then severed by the sharpened distal tip 61 of the cutting member 60 when the distal tip 61 of the cutting member contacts the fitting 50 distal the opening 23. The suture trimmer and the excess suture is then withdrawn from the tissue path, sheath, or cannula thereby leaving a suture loop having a knot and shortened suture tips extending from the knots. It is contemplated that the trimmed suture tail will have a length of about 1 mm to about 10 mm, more preferably between about 3 mm and about 7 mm is preferred to minimize the risks associated with lengths of suture that remain within the body as described above.

Although the present invention has been described in considerable detail with reference to certain preferred embodiments, it is contemplated that one skilled in the art may make modifications to the device herein without departing from the scope of the invention. Therefore, the scope of the appended claims should not be considered limited to the embodiments described herein

What is claimed is:

1. A suture trimmer comprising:
   a shaft having a first end, a second end, and a bore extending from the first end toward the second end, the shaft having an opening formed in a side adjacent the first end;

a cutting member slidably disposed within the bore of the shaft and movable between a first position where the opening is open and a second position where the opening is closed;

an actuating device in communication with the cutting member and operable to move the cutting member from the first position to the second position;

a snare housing removably coupled to the shaft; and a snare secured to the snare housing and extending through the opening and out of the bore at the first end of the shaft.

2. The suture trimmer according to claim 1, further comprising a biasing device the biasing device is coupled to the cutting member, wherein the biasing device retains the cutting member in the first position.

3. The suture trimmer according to claim 1, wherein the shaft is constructed of a bio-compatible material or a metal coated with a bio-compatible coating.

4. The suture trimmer according to claim 1, wherein the shaft is flexible.

5. The suture trimmer according to claim 1, wherein a distal end of the cutting member includes a sharpened edge configured to cut a suture passed through a portion of the bore and through the opening formed in the shaft.

6. The suture trimmer according to claim 1, wherein the first end is configured to receive and advance at least one knot formed with the suture.

7. The suture trimmer according to claim 1 wherein the snare has a diamond shaped portion.

8. The suture trimmer according to claim 1, wherein the snare comprises a nickel-titanium alloy.

9. A suture trimmer, the suture trimmer comprising:

a shaft having a first end, a second end and a bore extending axially therebetween, the shaft having an opening formed in a side adjacent the first end;

a fitting mounted to the first end of the shaft, the fitting comprising a protrusion that is at least partially received within the bore of the shaft and an aperture axially aligned with the bore of the shaft and in communication with the opening formed in the shaft; and a housing mountable to the shaft and receiving an actuating device in communication with a cutting member slidably disposed within the bore of the shaft, the cutting member configured to be moved between a first position and a second position, when disposed in the second position the cutting member closes the opening formed in the side of the shaft.

10. The suture trimmer according to claim 9, further comprising a biasing device disposed within the housing, the biasing device being coupled to the cutting member, wherein the biasing device retains the cutting member in the first position.

11. The suture trimmer according to claim 9, wherein the protrusion extends through the bore of the shaft and connects to the housing.

12. The suture trimmer according to claim 9, wherein a front face of the fitting is flat, concave, or convex.

13. The suture trimmer according to claim 9, wherein a front face of the fitting is disposed at an angle relative to the axis of the shaft.

14. The suture trimmer according to claim 9, further comprising a skive formed on the protrusion adjacent the aperture of the fitting.

15. The suture trimmer according to claim 9, further comprising a snare housing removably coupled to the shaft; and a snare secured to the snare housing and extending through the opening and out of the bore at the first end of the shaft.

* * * * *